US009274121B2

(12) United States Patent
Atapattu et al.

(10) Patent No.: US 9,274,121 B2
(45) Date of Patent: Mar. 1, 2016

(54) NON-FRET BOTULINUM ASSAY

(75) Inventors: Dhammika Atapattu, Madison, WI (US); Ward C. Tucker, Monona, WI (US)

(73) Assignee: BIOMADISON, INC., Del Mar, CA (US)

( * ) Notice: Subject to any disclaimer, the term of this patent is extended or adjusted under 35 U.S.C. 154(b) by 0 days.

(21) Appl. No.: 13/485,537

(22) Filed: May 31, 2012

(65) Prior Publication Data

US 2012/0309039 A1 Dec. 6, 2012

Related U.S. Application Data

(60) Provisional application No. 61/492,237, filed on Jun. 1, 2011.

(51) Int. Cl.
*C12Q 1/37* (2006.01)
*A61K 38/00* (2006.01)
*G01N 33/58* (2006.01)

(52) U.S. Cl.
CPC .......... *G01N 33/582* (2013.01); *G01N 2333/33* (2013.01)

(58) Field of Classification Search
None
See application file for complete search history.

(56) References Cited

U.S. PATENT DOCUMENTS

| 7,183,066 | B2 | 2/2007 | Fernandez-Salas et al. | |
|---|---|---|---|---|
| 7,208,285 | B2 | 4/2007 | Steward et al. | |
| 8,137,924 | B2 * | 3/2012 | Chapman et al. | 435/7.32 |
| 2004/0191887 | A1 | 9/2004 | Chapman et al. | |
| 2005/0214890 | A1 * | 9/2005 | Tan et al. | 435/23 |
| 2006/0134722 | A1 | 6/2006 | Chapman et al. | |
| 2009/0191583 | A1 | 7/2009 | Fernandez-Salas et al. | |
| 2011/0033866 | A1 | 2/2011 | Fish et al. | |

FOREIGN PATENT DOCUMENTS

| JP | 2007-520211 | 7/2007 |
|---|---|---|
| WO | 03/012393 | 2/2003 |
| WO | 2004/031355 | 4/2004 |
| WO | 2005/076785 | 8/2005 |

OTHER PUBLICATIONS

Clegg, R. et al. "How can One Choose the Best Method for Measuring FRET in a Microscope with My Biological System?" 2005 Microsc Microanal 11 (Suppl 2).*
Capek, P. et al., "Sensing the Deadliest Toxin: Technologies for Botulinum Neurotoxin Detection", Toxins, vol. 2, pp. 24-53, 2010.
Fang, H. et al., "A yeast assay probes the interaction between botulinum neurotoxin serotype B and its SNARE substrate", Proceedings of the National Academy of Sciences, vol. 103, No. 18, pp. 6958-6963, May 2, 2006.
Hunt, T. et al., "Characterization of SNARE Cleavage Products Generated by Formulated Botulinum Neurotoxin Type-A Drug Products", Toxins, vol. 2, pp. 2198-2212, 2010.
Ruge, D.R. et al., "Detection of six serotypes of botulinum neurotoxin using fluorogenic reporters", Analytical Biochemistry, vol. 411, pp. 200-209, 2011.
WIPO, "International Search Report", International Application No. PCT/US04/42366, Jul. 16, 2006.
WIPO, "International Search Report", International Application No. PCT/US03/30899, Jun. 9, 2004.

* cited by examiner

*Primary Examiner* — David J Steadman
*Assistant Examiner* — Paul Holland
(74) *Attorney, Agent, or Firm* — Fish & Tsang, LLP

(57) ABSTRACT

A composition includes an artificial construct having (a) a reporter-containing portion chemically coupled to (b) a cleavage site. The cleavage site interacts with an investigational substance in a manner that cleaves the reporter-containing portion from a remainder of the construct. The cleaved portion is destroyed or otherwise degraded by the local environment, and presence of an investigational substance is evidenced by reduction in signal from the reporter. The investigational substance is preferably a Botulinum toxin (BoTN), and the cleavage sequence is all or part of a SNARE protein. The cleavable reporter-containing portion is preferably Yellow Fluorescent Protein (YFP), Citrine, Venus, or a YPet protein.

19 Claims, 3 Drawing Sheets

NON-FRET BOTULINUM ASSAY

This application claims the benefit of priority to U.S. provisional patent application Ser. No. 61/492,237, filed Jun. 1, 2011. The priority application, along with all other publications referenced herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is protease assays, especially those related to Botulinum toxins.

BACKGROUND

Botulinum neurotoxins (BoNTs) are produced by *Clostridium botulinum*, and are among the most potent toxins known. These toxins are a well-recognized source of food poisoning, often resulting in serious harm or even death of the victims. There are seven structurally related botulinum neurotoxins or serotypes (BoNT/A-G), each of which is composed of a heavy chain (~100 KD) and a light chain (~50 KD). The heavy chain mediates toxin entry into a target cell through receptor-mediated endocytosis. Once internalized, the light chain is translocated from the endosomal vesicle lumen into the cytosol, and acts as a zinc-dependent protease to cleave proteins that mediate vesicle-target membrane fusion ("substrate proteins").

These BoNT substrate proteins include plasma membrane protein syntaxin, peripheral membrane protein SNAP-25, and a vesicle membrane protein synaptobrevin (Syb). These proteins are collectively referred to as the SNARE (soluble N-ethylmaleimide-sensitive factor attachment protein receptor) proteins. Cleavage of SNARE proteins blocks vesicle fusion with plasma membrane and abolishes neurotransmitter release at neuromuscular junction. Among the SNARE proteins, syntaxin and SNAP-25 usually reside on the target membrane and are thus referred to as t-SNAREs, while synaptobrevin is found exclusively with synaptic vesicles within the synapse and is called v-SNARE. Together, these three proteins form a complex that is thought to be the minimal machinery to mediate the fusion between vesicle membrane and plasma membrane. BoNT/A, E, and $C^1$ cleave SNAP-25, BoNT/B, D, F, G cleave synaptobrevin (Syb), at single but different sites. BoNT/C also cleaves syntaxin in addition to SNAP-25.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Due to their threat as a source of food poisoning, and as bioterrorism weapons, there is a need to sensitively and speedily detect BoNTs. Currently, the most sensitive method to detect toxins is to perform toxicity assay in mice. This method requires large numbers of mice, is time-consuming, and cannot be used to study toxin catalytic kinetics. A number of amplified immunoassay systems based on using antibodies against toxins have also been developed, but most such systems require complicated and expensive amplification process, and cannot be used to study toxin catalytic activity either. Although HPLC and immunoassay can be used to detect cleaved substrate molecules and measure enzymatic activities of these toxins, those methods are generally time-consuming and complicated, some of them require specialized antibodies, making them inapplicable for large-scale screening. Therefore, there is a need for new and improved methods and compositions for detecting BoNTs.

In the last few years, researchers have started investigating use of FRET assays to detect BoNTs. In FRET assays, two fluorigenic amino acid derivatives are used to replace two native amino acids in a short synthetic peptide (12-35 amino acids) that contain toxin cleavage sites. The fluorescence signal of one amino acid derivative is quenched by another amino acid derivative when they are close to each other in the peptide. This mechanism is called "Förster resonance energy transfer" (FRET). Cleavage of the peptide separates the two amino acid derivatives, such that a decrease in FRET can be detected.

FRET assays have been successfully used for detecting BoNTs. (See e.g., US Pat. App. No. 2004/0191887 to Chapman, filed Oct. 28, 2003, US Pat. App. No. 2006/0134722 to Chapman, filed Dec. 20, 2004, U.S. Pat. No. 7,208,285 to Steward (April 2007), U.S. Pat. No. 7,183,066 to Fernandez-Salas (February 2007), and application US2011/0033866 (publ. February 2010), Although some success has been demonstrated in applying FRET assays to detection of BoNTs, the sensitivity and specificity are still undesirable for many purposes.

In FRET assays for the localization of BoNT substrate proteins, for example, measurements relative to the loss of FRET emission upon cleavage of the peptide can suffer from severe interferences, such that in some cases there is no difference between cells treated with no BoNT versus cells treated with saturating concentrations of BoNT. Therefore, it can be said that methods based on the loss of FRET report BoNT induced changes very poorly and thus its low statistical performance and reproducibility render it a non-reliable methodology. The US application 2009/0191583 to Ester Fernandez-Salas claims a non-FRET BoNT assay using only a single fluorophore. The assays disclosed in this document use cells which are capable of efficient Clostridial toxin uptake and which include a membrane localized Clostridial toxin substrate containing a fluorescent marker.

As an example, a cell useful in this paper can express a $SNAP25_{206}$-enhanced green fluorescent protein (EGFP) fusion protein that localizes to the plasma membrane. Upon BoNT/A treatment of this cell, cleavage of the membrane localized $SNAP25_{206}$-EGFP substrate occurs, releasing the EGFP containing fragment into the cytoplasm. Upon excitation of the treated cell with a 484 nM laser, the EGFP is excited and emits light at 510 nM. However, because a portion of the EGFP is now cytoplasmic, a distribution change between the uncleaved, membrane localized $SNAP25_{206}$-EGFP toxin substrate and the cleaved, cytoplasmic localized EGFP fragment can be observed in BoNT/A treated cells. The assay might therefore work for qualitative analysis, but the presence of EGFP emitting portions in both the membrane and the cytoplasm renders this method undesirable for quantitative analysis.

Thus, improved apparatus, systems and methods are therefore still needed which overcome the drawbacks and the limits of the prior art relative to both FRET and non-FRET assays.

SUMMARY OF THE INVENTION

The present invention provides method and assays characterized in that a composition includes an artificial construct having (a) a reporter-containing portion chemically coupled to (b) a cleavage site that interacts with an investigational substance in a manner that cleaves the reporter-containing portion from a remainder of the construct. A particular class of embodiments is directed to a method for the qualitative and quantitative detection of a Botulinum toxin, comprising:

(i) providing a composition that includes an artificial construct and an enzyme, wherein the construct has (a) a reporter-containing portion and (b) a cleavage site that interacts with a portion of the Botulinum toxin in a manner that produces a cleavage of the reporter-containing portion from a remainder of the construct, wherein the composition exhibits emissions identifying a baseline signal; and wherein the enzyme facilitates degradation of the reporter-containing portion at least ten times faster after the cleavage than before the cleavage;

(ii) obtaining first emission measurements from said baseline signal (iii) exposing the composition to the Botulinum toxin; and then (iv) obtaining further emission measurements by testing the composition for a reduction of the baseline signal as an indication of the toxin cleaving the construct at the cleavage site, and degradation of the reporter-containing portion;

(v) comparing the first emission measurements of step (ii) with the further measurements of step (iv).

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Furthermore, the inventive subject matter relates also to an assay for testing presence of an investigative substance, comprising a cell having an artificial construct and an enzyme, wherein the construct has a protected portion and a protecting portion, selected such that the protected portion includes a reporter, and the investigative substance acts to de-protect the protected portion in vitro, wherein the enzyme facilitates degradation of the protected portion at least ten times faster when de-protected than when protected, thereby reducing a signal obtainable from the reporter which is used for the quantitative determination of the investigative substance.

The cleaved reporter-containing portion is destroyed or otherwise degraded by the local environment, and presence of the investigational substance is then evidenced by reduction in signal from the reporter. In the context of this application, it is contemplated that degradation of the protected portion will typically intracellularly by at least one of two pathways, by the ubiquitin-dependent process that targets proteins to the proteasome, or by the autophagy-lysosomal pathway. In one pathway, the proteasome is the enzyme. In the lysome pathways, it is contemplated that the enzymes of interest are hydrolases, including especially a family of proteases called the cathepsins.

In preferred embodiments, the investigational substance is a Botulinum toxin (BoTN), and the cleavage sequence is appropriately matched with the investigational substance. For example, the BoNT/A, E, and C cleave SNAP-25, and BoNT/B, D, F, G cleave synaptobrevin (Syb), at single but different sites. BoNT/C also cleaves syntaxin in addition to SNAP-25.

Contemplated cleavage site sequences can advantageously comprise (a) a SNARE protein, motif, or mutein. "Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

In other aspects of preferred embodiments, the cleavable reporter-containing portion comprises a fluorescent protein, as for example, Yellow Fluorescent Protein (YFP). YFP is a genetic mutant of green fluorescent protein, derived from Aequorea Victoria, and has an excitation peak is 514 nm and emission peak is 527 nm.

Also contemplated for use in the cleavable reporter-containing portion are the closely related Citrine, Venus, and YPet proteins. The modifications have reduced chloride sensitivity, faster maturation, and increased brightness (product of the extinction coefficient and quantum yield). Of course, any of the fluorescent proteins mentioned herein can be modified to include specific characteristics (e.g., spectral) or be truncated to a specific size.

Upon cleavage, the construct is cleaved into two parts, a reporter containing portion that is destroyed or otherwise degraded by the cytosol or other local environment, and a second portion. To normalize the signal detection, that second portion can advantageously include a second fluorescent protein, preferably at an opposite end from the reporter, which can assist in normalizing the assay. The second fluorescent protein can, for example, be Cyan Fluorescent Protein (CFP), mCherry, or mStrawberry. The reporter-containing portion is not coupled with the second fluorophore in a manner that produces Förster resonance energy transfer (FRET).

Thus, prior to exposure of the construct to BoTN or other cleaving substance, the composition containing the construct (whether cell-based or otherwise) exhibits a baseline signal, and then after exposure exhibits a reduced signal. For the measurement of YFP degradation, directly, separately excited YFP emissions (top, Ex500, Em526) and CFP emissions (middle, Ex434, Em470) are collected. Those emissions are then background subtracted and the YFP emission is divided by CFP emission to control for cell density and reporter expression in the individual cells. That emission ratio (YFP/CFP, bottom) is how the assay is reported.

Destruction or other degradation of the reporter-containing portion takes place at a much faster rate post-exposure to BoTN than pre-exposure. In preferred embodiments, it is contemplated that the destruction or other degradation of the reporter containing portion occurs at least 2× (twice) as fast post-exposure as pre-exposure, but more preferably the rate post-exposure rate is at least 5×, at least 10×, at least 100× relative to the pre-exposure rate.

In yet other aspects of preferred embodiments, the local environment is the cytosol of a living cell. For example, YFP can be used as the C-terminal fluorophore, and CFP can be used the N-terminal fluorophore. Experimental work has now verified that in the absence of BoNT/A, YFP can be directly excited and the emission collected. The excitation occurs typically at 505 nM and the corresponding emission at 527 nM. In the presence of BoNT/A, the reporter is cleaved releasing a fragment containing YFP. That fragment is degraded by the cell, destroying the YFP and its emission. Thus, BoNT/A activity is detected by measurements relative to the loss in YFP emission. No FRET is therefore required, what avoids all the limits and the problems indicated above.

Hybrid protein(s) that are formed in the transfected cells preferably include a transmembrane domain, which tends to locate to intracellular vesicles, and thereby present a vesicle-bound substrate. Heavy chain-mediated endocytosis of the BoNT into the transfected cell is followed by presentation of the light chain on the outer surface of the vesicle, allowing the protease activity of the light chain to cleave the cleavage sequence of the hybrid protein(s), thus cleaving the reporter-containing portion, which then is destroyed or degraded to reduce the signal being tested. Full-length Syb, for example, contains 116 amino acids, and is localized to vesicles through a single transmembrane domain. In some contemplated assays, the membrane-anchoring domain comprises a fragment that contains a palmitoylation site. Suitable membrane-anchoring domains are described, for example, in US 20060134722 to Chapman.

While it is especially preferred that the transmembrane domain is the transmembrane domain of synaptobrevin, mutations (e.g., transitions, transversions, insertions, deletions, inversions, etc.) thereof, and even non-synaptobrevin transmembrane domains are also deemed suitable for use herein. Similarly, it should be appreciated that the transmembrane domain may also be replaced by another polypeptide moiety that allows at least temporary anchoring of the hybrid protein to a membrane such that the remainder of the hybrid protein is exposed to the cytosol.

With respect to the transfected cells expressing the hybrid protein it is generally preferred that the cell is stably transfected. Nevertheless, transient transfection is also contemplated. It is still further typically preferred that the transfected cell is a neuronal cell. However, numerous other non-neuronal cells (including mammalian, rodent, and insect cells, and even yeast and bacterial cells) are also contemplated herein. Most typically, the cells will constitutively express the hybrid protein(s) are therefore under appropriate regulatory elements. In alternative aspects, the expression may also be induced.

According to a preferred embodiment, a recombinant nucleic acid molecule, preferably an expression vector, encoding a BoNT substrate polypeptide and a suitable reporter is introduced into a suitable host cell. An ordinarily skilled person can choose a suitable expression vector, preferably a mammalian expression vector, and will recognize that there are enormous numbers of choices. For example, the pcDNA series of vectors, such as pCI and pSi (from Promega, Madison, Wis.), CDM8, pCeo4. Many of these vectors use viral promoters. Preferably, inducible promoters are used, such as the tet-off and tet-on vectors from Clontech (Mountain View, Calif.).

Many choices of cell lines are suitable as the host cell. Preferably, the cell is of a type in which the respective BoNT exhibits its toxic activities. In other words, the cells preferably display suitable cell surface receptors, or otherwise allow the toxin to be translocated into the cell sufficiently efficiently, and allow the toxin to cleave the suitable substrate polypeptide. Specific examples include primary cultured neurons (cortical neuron, hippocampal neuron, spinal cord motor neuron, etc); PC12 cells or derived PC12 cell lines; primary cultured chromaffin cells; several cultured neuroblastoma cell lines, such as murine cholinergic Neuro 2a cell line, human adrenergic SK-N-SH cell line, and NS-26 cell line. See e.g. Foster and Stringer (1999), Genetic Regulatory Elements Introduced Into Neural Stem and Progenitor Cell Populations, Brain Pathology 9: 547-567.

The coding region for the reporter/cleavage site construct is under the control of a suitable promoter. Depending on the types of host cells used, many suitable promoters are known and readily available in the art. Such promoters can be inducible or constitutive. A constitutive promoter may be selected to direct the expression of the desired polypeptide. Such an expression construct may provide additional advantages since it circumvents the need to culture the expression hosts on a medium containing an inducing substrate. Examples of suitable promoters would be LTR, SV40 and CMV in mammalian systems; *E. coli* lac or trp in bacterial systems; baculovirus polyhedron promoter (polh) in insect systems and other promoters that are known to control expression in eukaryotic and prokaryotic cells or their viruses. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), .alpha.-amylase (amy), amyloglucosidase (AG—from the glaA gene), acetamidase (amdS) and glyceraldehyde-3-phosphate dehydrogenase (gpd) promoters. Examples of strong yeast promoters are those obtainable from the genes for alcohol dehydrogenase, lactase, 3-phosphoglycerate kinase and triosephosphate isomerase. Examples of strong bacterial promoters include $SPO_2$ promoters as well as promoters from extracellular protease genes.

Hybrid promoters may also be used to improve inducible regulation of the expression construct. The promoter can additionally include features to ensure or to increase expression in a suitable host. For example, the features can be conserved regions such as a Pribnow Box or a TATA box. The promoter may even contain other sequences to affect (such as to maintain, enhance or decrease) the levels of expression of the nucleotide sequence. For example, suitable other sequences include the Shl-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat, 1987, Gene 217: 217-225; and Dawson, 1993, Plant Mol. Biol. 23: 97).

The expression vector may also contain sequences which act on the promoter to amplify expression. For example, the SV40, CMV, and polyoma cis-acting elements (enhancer) and a selectable marker can provide a phenotypic trait for selection (e.g. dihydrofolate reductase or neomycin resistance for mammalian cells or amplicillin/tetracyclin resistance for *E. coli*). Selection of the appropriate vector containing the appropriate promoter and selection marker is well within the level of those skilled in the art.

Preferably, the coding region for the construct is under the control of an inducible promoter. In comparison to a constitutive promoter, an inducible promoter is preferable because it allows for suitable control of the concentration of the reporter in the cell, therefore the measurement of changes in signals are greatly facilitated.

For example, expression can be controlled using the Tet-on & Tet-off system Clontech (Mountain View, Calif.). Under the control of this promoter, gene expression can be regulated in a precise, reversible and quantitative manner. Briefly, for Tet-on system, the transcription of downstream gene only happens when doxycycline is present in the culture medium. After the transcription for a certain period of time, one can change culture medium to deplete doxycycline, thus, stop the synthesis of new reporter proteins. Therefore, there is no background from newly synthesized reporter proteins, and one may be able to see a faster change after toxin treatment.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy emission can be carried out with an argon ion laser, a high intensity mercury (Hg) arc lamp, a fiber optic light source, or other high intensity light source appropriately filtered for excitation in the desired range. It will be apparent to those skilled in the art that excitation/detection means can be augmented by the incorporation of photomultiplier means to enhance detection sensitivity. For example, the two photon cross correlation method may be used to achieve the detection on a single-molecule scale (see e.g. Kohl et al., Proc. Nat'l. Acad. Sci., 99:12161, 2002).

Local environments for the construct other than living cells are also contemplated, including for example, cytosol of lysed cells, and synthetic media that contains one or more enzymes capable of degrading the cleavable fragment when cleaved from the reporter molecule, but incapable or much less capable of degrading the cleavable fragment prior to cleavage from reporter molecule.

It is further contemplated to provide an isolated polynucleotide molecule encoding a construct described above. The construct is preferably an expression vector comprising the polynucleotide molecule operably linked to a promoter. A preferable promoter is an inducible promoter.

In a further embodiment, a kit comprises a construct as contemplated herein, in a suitable container.

The inventive subject matter also provides a method for screening for an inhibitor of a botulinum neurotoxin, comprising providing a cell genetically engineered to express a construct as described above, exposing said cell to the botulinum neurotoxin in the presence of a candidate inhibitor compound; and detecting a fluorescent or other signal of the cell before and after said exposing to the botulinum toxin, and comparing the signal to that of a cell exposed to the botulinum neurotoxin in the absence of the candidate inhibitor. To the extent that signal reduction was circumvented, the candidate inhibitor would be considered capable of inhibiting the botulinum neurotoxin. In some contemplated embodiments, the candidate compound could be a member of a library of compounds, and the method could be a high throughput method.

BRIEF DESCRIPTION OF THE DRAWINGS

FIG. 2A shows photomicrographs of transformed cells and transformed cells following exposure to BoNT/A. FIG. 2B graphically depicts results of fluorescence emissions measurements from transformed cells exposed to BoNT/A and control transformed cells. FIG. 2C shows results of SDS-PAGE followed by immunoblotting and probing with anti-SNAP-25 of the products of exposure of various constructs to BoNT/A.

DETAILED DESCRIPTION

Various objects, features, aspects and advantages of the inventive subject matter will become more apparent from the following detailed description of preferred embodiments, along with the accompanying drawing figures in which like numerals represent like components.

Figure 1:
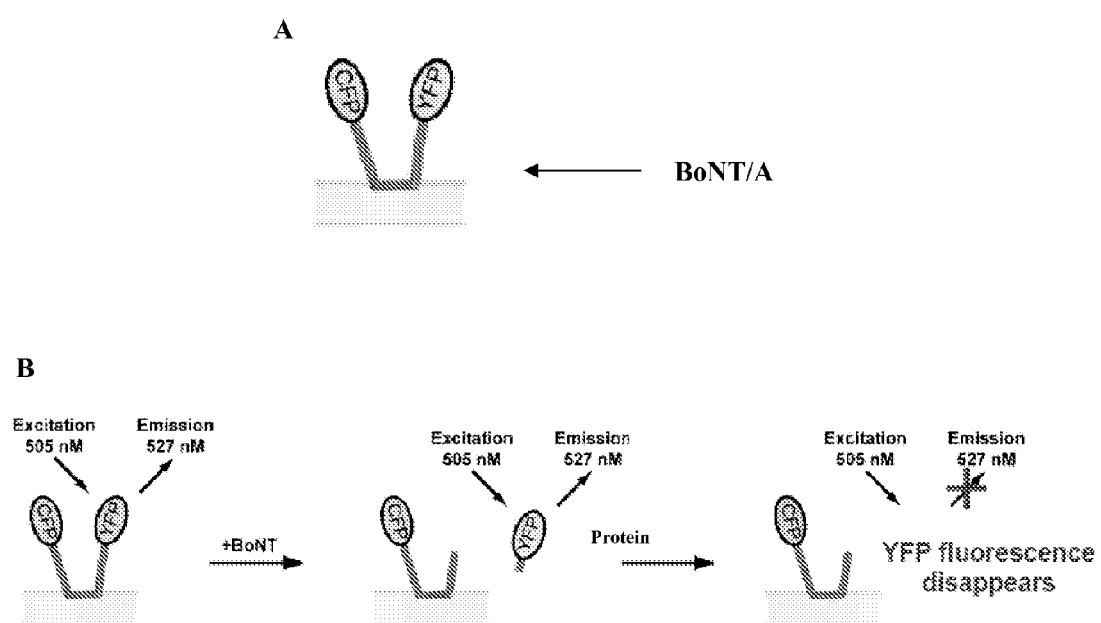
FIG. 1 schematically depicts an exemplary construct and method of the inventive concept.

FIG. 1 diagrams an exemplary assay in which BoNT/A cell-based reporters are used to detect BoNT/A activity by loss of YFP fluorescence.

(A) BioSentinel's BOCELL™ A BoNT/A construct. The reporter fluorophore, YFP, and the normalization fluorophore, CFP, are coupled by a cleavage sequence, SNAP-25 (green). SNAP-25 palmitoylation localizes the reporter to a plasma membrane.

(B) Detection of BoNT/A activity by loss of YFP fluorescence. The YFP moiety is directly excited leading to fluorescence emission in the absence of BoNT/A. Cleavage of the reporter by BoNT/A releases a C-terminal reporter fragment containing the YFP moiety into the cytosol. The fragment is rapidly degraded and, thus, YFP emission is lost. The CFP signal is still used to control for cell-to-cell reporter expression levels and cell density.

Figure 2:
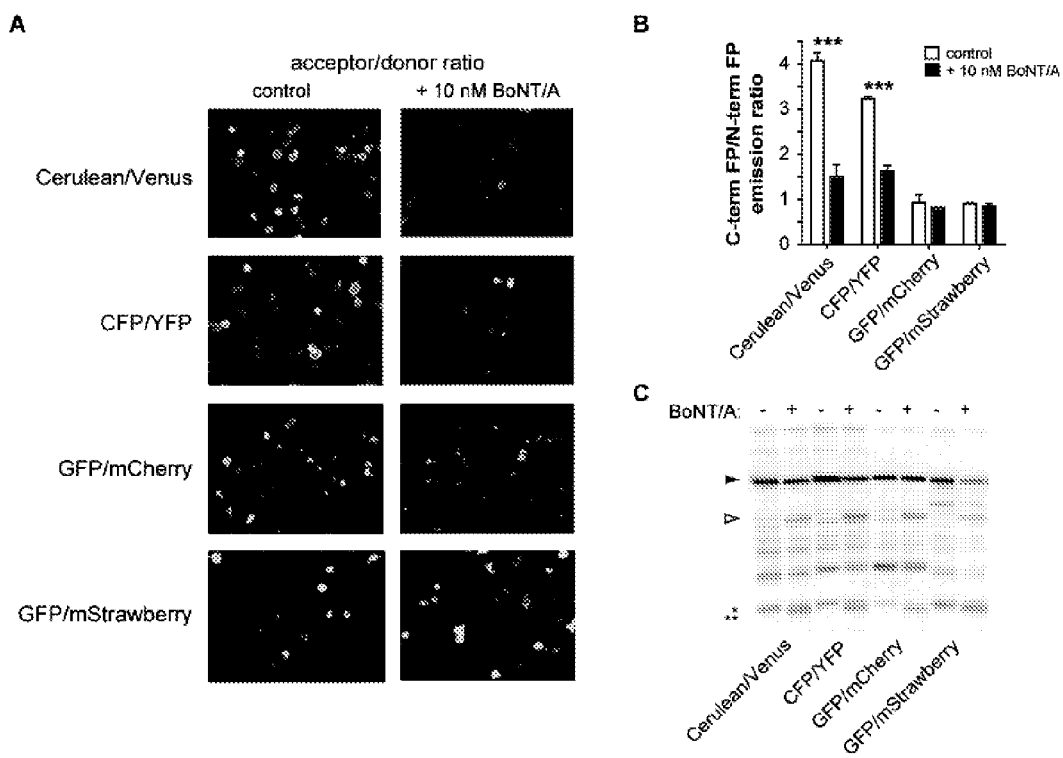
FIGS. 2A, 2B, and 2C depict results obtained from testing of different reporting constructs.

Surprisingly, not all fluorescent proteins related to YFP are effective as the reporter fluorophore. For example, FIG. 2 provides evidence that reporters containing YFP or the closely related derivative Venus can detect BoNT/A activity in cells, but not mCherry or mStrawberry. Here, Neuro2A cells were grown in a 96-well plate to 70% confluency and transiently transfected using LIPOFECTAMINE™2000 (INVITROGEN™), with reporters containing the indicated N-terminal and C-terminal (N-term/C-term) fluorophore pairs. After 24 h, cells were incubated in the presence or absence of 10 nM BoNT/A at 37° C. for 72 h in 100 µl of phenol red-free MEM medium.

FIG. 2A shows BoNT/A-induced changes in fluorescence responses. Semi-automated YFP and CFP fluorescence measurements were performed using a NIKON™ TE2000-U fluorescent microscope with 20× magnification and NIKON™ NIS Elements 3.4 software. Shown are randomly selected fields pseudo-colored for the C-terminal/N-terminal fluorescent protein (FP) fluorescence ratio. Ratios were calculated from emissions collected upon direct excitement of each fluorophore.

FIG. 2B represents fluorescence ratios and BoNT/A sensitivities of the cell-based reporters. 30 randomly selected cells per condition were analyzed for fluorescence ratios in the presence or absence of 10 nM BoNT/A. The average signal from the 30 cells from 5 microscopic fields on 3 different wells is shown. Cells exhibiting over-saturated fluorescence were excluded.

FIG. 2C. This is a blot showing that BoNT/A was active in cells regardless of the reporter. All reporters show some cleavage in the presence of BoNT/A, and all native SNAP25s are cleaved. Cells were transfected and treated with BoNT/A as described above but scaled up into 6-well plates. After 72 h incubation with BoNT/A, cells were washed 3× with serum-free MEM, collected by scraping, and lysed using M-Per Lysis Buffer (Pierce™). 40 µg of cell lysate was subjected to SDS-PAGE before transfer to nitrocellulose paper and immunoblot analysis using an antibody directed against SNAP-25 (clone 71.2, Synaptic Systems). Arrows indicate the position of the full-length (closed) and cleaved (open) forms of the reporters. Full-length (*) and cleaved (**) native SNAP-25 are indicated.

Viewed from another perspective, the inventive subject matter can be extended beyond cleavable substrates, to any assay having a construct with a reporter that can be de-protected, and then degraded in some manner by the cytosol or other local environment. For example, a susceptible reporter could be modified to include a 'bait' domain that is used to screen against a library of recombinant proteins that could possibly bind with the bait domain. Without the bait domain protected by a binding protein, the susceptible reporter will be degraded. In such an assay, cells expressing binding proteins will form a complex to protect the susceptible reporter from degradation, while cells expressing a binding partner to the bait will light up. The bait domain could advantageously be a small peptide, and the binding partners could be members of a library of proteins (or protein mutants). The system could also be reversed such that there is a library of bait domains tested against a single test protein (or test protein library).

In each of these instances it is considered advantageous to include a second reporter that is not degraded post-exposure by the cytosol or other local environment, or is at least degraded much more slowly post-exposure than the first reporter.

Still further, whereas the reporter can conveniently be selected from suitable fluorophores, it is contemplated that the reporter could be replaced or augmented by any other protein or other component with a defined function that is known to (a) have a relatively fast turnover in the cell without protection, and (b) that can be protected by interaction with a binding partner. Defined functions include transcription activators for reporter gene, repressors for lethal genes, etc (anything that can be easily identified or selected against).

Figure 3:
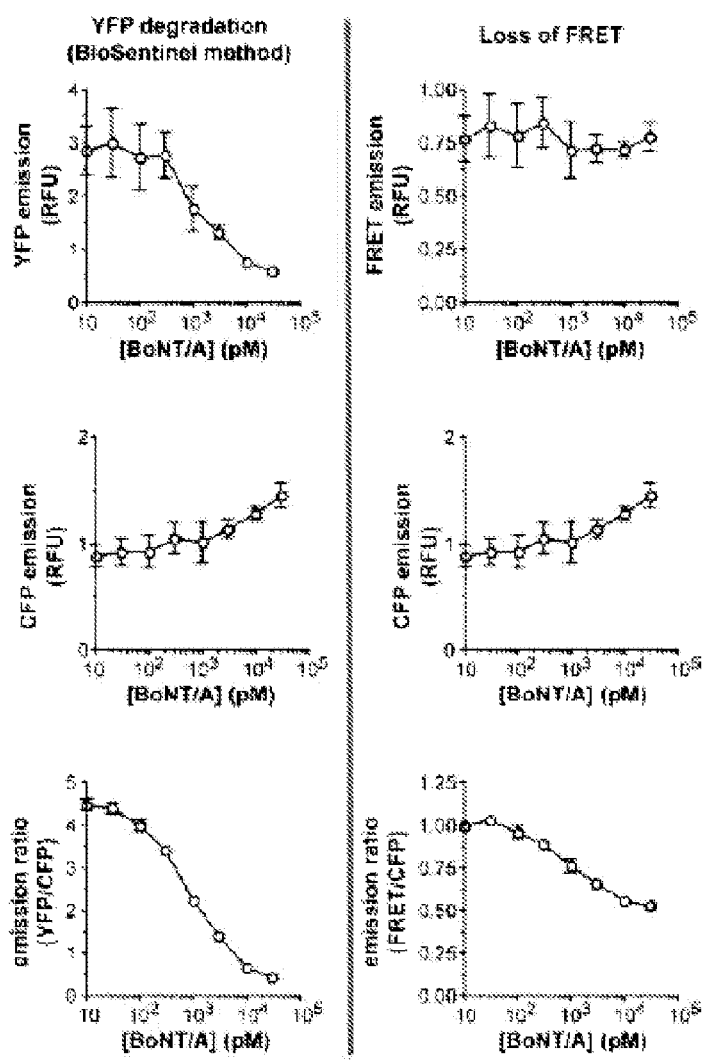
FIG. 3 graphically depicts the results of fluorescence measurements from transformed cells expressing a reporting construct of the inventive concept. Results from the same set of cells are shown for the BioSentinel method (based upon characterization of YFP degradation) on the left, and for the prior art method based on FRET emission (Loss of FRET) from the construct on the right.

FIG. 3. In this embodiment, Data was collected for both YFP degradation and loss of FRET according to the state of the art practice from the exact same plates of cells. For YFP degradation, directly and singularly excited YFP emissions (top, Ex500, Em526) and CFP emissions (middle, Ex434, Em470) are collected. Those emission are then background subtracted and the YFP emission is divided by CFP emission to control for cell density and reporter expression in the individual wells. That emission ratio (YFP/CFP, bottom) is then used for the essay report.

For loss of FRET, FRET emissions (top, Ex434, Em526) and CFP emissions (middle, Ex434, Em470) are collected. Those emissions are then background subtracted, and the FRET emission is divided by CFP emission to control for cell density and reporter expression in the individual wells. That emission ratio (FRET/CFP, bottom) is shown here to compare to the normal method.

The key comparison is the loss of directly excited YFP versus the loss of FRET emission. From the comparison between the measurements and the corresponding curves, it becomes immediately apparent that the overall dynamic range for YFP degradation is much larger than the dynamic range of loss of FRET emissions. In some cases, there is no difference, statistically, between cells treated with no BoNT versus sells treated with saturating concentrations of BoNT when looking solely at the raw FRET emissions. For the loss of FRET method, the BoNT dose response only becomes clear after dividing the FRET emission by the CFP (donor) emission. The CFP (donor) emission shows a small increase emission due to de-quenching in response to reporter cleavage.

In summary, the loss of FRET method reports BoNT-induced changes in the reporter very poorly, or not at all, and therefore cannot be therefore used for a correct qualitative and quantitative determination. In contrast, preferred methods contemplated herein have a high degree of specificity and reproducibility, which allow one to rely on the data for both the qualitative and quantitative analysis.

Genetic Construction of Alternative Reporters

Twenty alternate fluorophore constructs were generated in four plasmid backgrounds. Below is the internal name of each construct with a brief description of the background and cloned fragment. A more detailed summary of the construction methods follows.

| Construct Name | Plasmid Background | Description | Alternative Reporter Mechanism |
|---|---|---|---|
| pMD0076a | pcDNA4/TO | mRaspberry-SNAP-YFP | 1 |
| pMD0076b | pcDNA4/TO | mCherry-SNAP-YFP | 1 |
| pMD0077 | pIRES | SNAP-YFP, CFP | 3 |
| pMD0078 | pECFP-C1 (Modified) | Synapsin promoter, SNAP-YFP | 2 |
| pMD0079 | pcDNA4/TO | SNAP-YFP | 2 |
| pMD0080 | pECFP-C1 (Modified) | SNAP-YFP | 2 |
| pMD0081 | pECFP-C1 (Modified) | mRaspberry-SNAP-YFP | 1 |
| pMD0082 | pECFP-C1 (Modified) | mCherry-SNAP-YFP | 1 |
| pMD0090 | pIRES | SNAP-Venus, CFP | 3 |
| pMD0091 | pcDNA4/TO | SNAP-Venus | 2 |
| pMD0092 | pECFP-C1 (Modified) | SNAP-Venus | 2 |
| pMD0097 | pcDNA4/TO | mKate2-SNAP-YFP | 1 |
| pMD0098 | pcDNA4/TO | TagRFP-SNAP-YFP | 1 |
| pMD0099 | pECFP-C1 (Modified) | mKate2-SNAP-YFP | 1 |
| pMD0100 | pECFP-C1 (Modified) | TagRFP-SNAP-YFP | 1 |
| pMD0103 | pBudCE4.1 | SNAP-YFP, CFP | 3 |
| pMD0104 | pBudCE4.1 | SNAP-YFP, mRaspberry | 3 |
| pMD0105 | pBudCE4.1 | SNAP-YFP, mCherry | 3 |
| pMD0106 | pBudCE4.1 | SNAP-Venus, CFP | 3 |
| pMD0107 | pBudCE4.1 | SNAP-Venus, mRaspberry | 3 |
| pMD0108 | pBudCE4.1 | SNAP-Venus, mCherry | 3 | pMD0076a, pMD0076b, pMD0097, and pMD0098

Constructs were generated by amplifying the mRaspberry, mCherry, mKate2, and TagRFP fluorophores with engineered KpnI and XhoI restriction sites. The amplified fragments and the previously used pcDNA4/TO BOCELL™ vector generated were then digested with KpnI/XhoI. The vector DNA, minus the excised CFP, was then ligated with the mRaspberry, mCherry, mKate2, and TagRFP fragments to create the final vectors.

pMD0079 and pMD0091

For pMD0079, SNAP YFP was amplified with engineered BamHI and XhoI restriction sites. The amplified fragment and pcDNA4/TO vector DNA were then digested with BamHI/XhoI and then ligated together. pMD0091 was then generated by amplifying the Venus fluorophore with engineered EcoRI and XbaI restriction sites. The amplified Venus fragment and pMD0079 were then digested with EcoRI/XbaI. The pMD0079 vector DNA, minus the excised YFP, was then ligated with the Venus fragment to create pMD0091.

pMD0077 and pMD0090

For pMD0077, SNAP YFP was amplified with engineered NheI and XhoI restriction sites. The amplified fragment and pIRES vector DNA were then digested with NheI/XhoI and then ligated together. The CFP fluorophore was then amplified with engineered XbaI/NotI restriction sites. The amplified fragment and previously generated SNAP YFP-containing pIRES vector were then digested with XbaI/NotI and ligated together to create pMD0077. pMD0090 was then generated by amplifying the Venus fluorophore with engineered EcoRI and MluI restriction sites. The amplified Venus fragment and pMD0077 were then digested with EcoRI/MluI. The pMD0077 vector DNA, minus the excised YFP, was then ligated with the Venus fragment to create pMD0090.

pMD0078 and pMD0080

For pMD0080, SNAP YFP was amplified with engineered NheI and XhoI restriction sites. Then amplified fragment and pECFP-C 1 were then digested with NheI/XhoI. The vector DNA, minus the excised CFP, was then ligated with the SNAP YFP to create pMD0080. pMD0078 was then generated by amplifying the synapsin promoter with engineered AseI and NheI restriction sites. The amplified fragment and pMD0080 were then digested with AseI/NheI. The pMD0080 vector DNA, minus the excised CMV promoter, was then ligated with the synapsin promoter to create pMD0078.

pMD0081, pMD0082, pMD0099, pMD0100

Constructs were generated by amplifying the mRaspberry, mCherry, mKate2, and TagRFP fluorophores with engineered NheI and XhoI restriction sites. The amplified fragments and original BOCELL™ construct from Min (pECFP-C1 background) were then digested with NheI/XhoI. The BOCELL™ construct, minus the excised CFP fragment, was then ligated with the mRaspberry, mCherry, mKate2, and TagRFP fragments to create pMD0081, pMD0082, pMD0099, and pMD0100.

pMD0092

For pMD0092, the Venus fluorophore was amplified with engineered EcoRI and XbaI restriction sites. The amplified fragment and pMD0080 were then digested with EcoRI/XbaI. The pMD0080, minus the excised YFP fragment, was then ligated with the Venus fragment to generate pMD0092.

pMD0103, pMD0104, and pMD0105

The SNAP YFP construct was amplified with engineered XbaI and BamHI restriction sites. The amplified fragment and pBudCE4.1 vector were then digested with XbaI/BamHI and ligated together. The CFP, mRaspberry, and mCherry fluorophores were then amplified with engineered KpnI and BglII restriction sites. The amplified fragments and previously generated pBudCE4.1 vector containing SNAP YFP were then digested with KpnI/BglII and ligated together to generate pMD0103, pMD0104, and pMD0105.

pMD0106, pMD0107, and pMD0108

The SNAP Venus construct was amplified with engineered XbaI and BamHI restriction sites. The amplified fragment and pBudCE4.1 vector were then digested with XbaI/BamHI and ligated together. The CFP, mRaspberry, and mCherry fluorophores were then amplified with engineered KpnI and BglII restriction sites. The amplified fragments and previously generated pBudCE4.1 vector containing SNAP Venus were then digested with KpnI/BglII and ligated together to generate pMD0106, pMD0107, and pMD0108.

Primary Screening of the Alternative Reporters

Neuro2A cells were seeded into 96-well plates and allowed to expand 24-48 h before transiently transfecting the cells using the above genetic constructs and LIPOFECTAMINE™ 2000according to the manufacturer's instructions. Transfected cells were allowed to recover for 24 hr before applying 0 or 30 nM BoNT/A holotoxin and incubating the cells an additional 24 hr at 37° C., 5% $CO_2$. Cells were then imaged using a NIKON™-TE2000U fluorescence microscope taking a minimum of three images per condition. Fluorescence emissions were collected using filters appropriate for the listed fluorophores. Total fluorescence emissions were also collected using a Varioskan™ fluorescence microplate reader using appropriate excitation and emission wavelength settings.

Fluorescence microscopy data was processed to gate out over expressing (saturated) cells based on pixel intensities for a given channel. Total emissions from each channel were then collected and, when indicated, the BoNT/A-responsive YFP or Venus emissions were divided by the BoNT/A-unresponsive CFP, RFP (mKate2, mRaspberry, or mCherry), or exogenously added membrane dye (Alternative Reporter 2) emissions.

Each reporter construct, using the data collected above, was analyzed for the following: Cellular targeting of each reporter was judged by the presence of uniform fluorescence expression on the plasma membrane. Poor plasma membrane targeting was associated with the presence of bright, punctate spots within the cell. Reporters lacking plasma membrane targeting were eliminated from further consideration. Total fluorescence emissions and, thus total reporter expression, were judged by the emissions of a given fluorescent probe relative to background emissions. Probes that did not give a signal >2 times that of background were eliminated from further consideration.

Secondary Screening of the Alternative Reporters: BoNT/A-Dose Responses

Genetic constructs that passed primary screening were transiently transfected into cells as described above but using varying DNA concentrations. Varying the DNA concentration generated cells with varying levels of reporter expression. After transfection and a 24 hr recovery period, the transfected cells were titrated with 10 pM to 30 nM BoNT/A allowed to further incubate. After incubation, fluorescence emissions were collected using a Varioskan fluorescence microplate reader using appropriate excitation and emission wavelength settings. For all experiments, test reporter responses were directly compared to the current BOCELL™ reporter CFP-SNAP25-YFP that was transiently transfected in parallel.

Fluorescence emissions for the BoNT/A-response YFP were divided by the BoNT/A-unresponsive CFP, RFP (mKate2, mRaspberry, or mCherry), or exogenously added membrane dye (Alternative Reporter 2) emissions generating an emission ratio. The emission ratio was then plotted as a function of BoNT/A concentration. Data was compared to the BOCELL™ reporter. Test reporter suitability was qualitatively assessed by comparison to the BOCELL™ reporter: Does BoNT/A elicit a similar response with the test reporter compared to the current BOCELL™ reporter?

Secondary Screening of the Alternative Reporters: FRET Emissions

Reporter genetic constructs were transfected into cells plated on glass cover slips using LIPOFECTAMINE™ according to the manufacturer's protocol. For each construct, single fluorophore controls were also transfected. After a 24 hr recovery period, cells were treated with or without 30 nM BoNT. Using the controls for each reporter, images were captured by fluorescence microscopy and the images used to calibrate FRET determinations by a three-filter set method. Reporters were then evaluated for FRET efficiency in the presence and absence of BoNT/A. For all experiments, test reporter responses were directly compared to the current BOCELL™ reporter CFP-SNAP25-YFP that was transiently transfected in parallel. Each test reporter was evaluated for the presence of FRET and whether FRET emissions were responsive to BoNT/A. The conclusion was that FRET emissions do not represent a reliable screening method, in line with the conditions already observed in example 3.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method for the qualitative and quantitative detection of a Botulinum toxin, comprising in sequence:
   (i) providing a composition that includes an artificial construct and an enzyme,
   wherein the construct has (a) a reporter-containing portion comprising a first fluorophore that is degraded by the enzyme, (b) a cleavage site comprising at least a portion of a motif selected from the group consisting of SNAP-25, synaptobrevin, and syntaxin, wherein the motif interacts with a portion of the Botulinum toxin in a manner that produces a cleavage of the first fluorophore from a remainder of the construct, and (c) a second portion comprising a second fluorophore, wherein the cleavage site is interposed between the reporter containing portion and the second portion;
   (ii) obtaining a baseline signal emission measurement from the construct;
   (iii) exposing the Botulinum toxin composition to the composition; and
   (iv) obtaining a further emission measurement from the reporter fluorophore,
   wherein the reporter-containing portion and the second portion are positioned in the construct such that FRET emission from the first fluorophore does not show a decreasing trend relative to increasing concentrations of the Botulinum toxin composition, and wherein a normalization emission measurement is obtained from the second fluorophore.

2. The method of claim 1 wherein the first fluorophore comprises Yellow Fluorescent Protein (YFP).

3. The method of claim 1 wherein the first fluorophore is selected from the group consisting of Yellow Fluorescent Protein (YFP), Citrine, Venus, and a YPet protein.

4. The method of claim 1 wherein the first fluorophore is a derivative of at least one of Yellow Fluorescent Protein (YFP), Citrine, Venus, and a YPet protein.

5. The method of claim 1 wherein the second fluorophore is at an opposite end of the construct from the reporter-containing portion.

6. The method of claim 1 wherein the first fluorophore comprises Yellow Fluorescent Protein (YFP), and second fluorophore comprises Cyan Fluorescent Protein (CFP).

7. The method of claim 1 6 wherein the first fluorophore comprises at least one of Yellow Fluorescent Protein (YFP), Citrine, Venus, and a YPet protein, and the second fluorophore comprises at least one of CFP, mStrawberry, and mCherry.

8. The method of claim 1 wherein the first fluorophore comprises a chromophore.

9. The method of claim 1 wherein the construct is produced endogenously by a living transfected cell.

10. The method of claim 1 wherein the composition is contained in a living transfected cell, the first fluorophore comprises at least one of Yellow Fluorescent Protein (YFP), Citrine, Venus, and a YPet protein, and wherein the second fluorophore comprises a second fluorescent protein.

11. The method according to any one of the preceding claims, wherein the baseline emission measurements of step (ii) are obtained by directly exciting the second fluorophore.

12. The method of claim 1, wherein a measurement of first fluorophore degradation is obtained by collecting emissions of directly, separately excited first fluorophore and second fluorophore.

13. The method of claim 9, wherein the fluorescent emission of the second fluorophore is used to correct for variations in-cell density and reporter expression in the individual cells.

14. An assay for testing presence of an investigative substance, comprising a cell having an artificial construct and an enzyme, wherein the construct has a protected portion and a protecting portion, selected such that the protected portion includes a first reporter and the protecting portion includes a second reporter, and the investigative substance acts to deprotect the protected portion in vitro, wherein the enzyme facilitates degradation of the protected portion, thereby reducing a signal obtainable from the first reporter, which is used for the quantitative determination of the investigative substance, wherein the first reporter and the second reporter are positioned such that FRET emission from the first reporter does not show a decreasing trend relative to increasing concentrations of the investigative substance and wherein a normalization emission measurement is obtained from the second reporter.

15. The assay of claim 14, wherein the first reporter comprises a fluorophore preferably being at least one of Yellow Fluorescent Protein (YFP), Citrine, Venus, and a YPet protein, and a cleavage site comprising at least a portion of a motif selected from the group consisting of SNAP-25, synaptobrevin, and syntaxin, wherein the motif interacts with a portion of the Botulinum toxin in a manner that produces a cleavage of at least a portion of the protected portion from a remainder of the construct.

16. The assay of claim 15, wherein the second reporter is selected from the group comprising CFP, mStrawberry, and mCherry.

17. The assay of claim 15, wherein the construct contains a membrane-localizing domain, and the enzyme exists in the cytosol of the cell.

18. The assay of claim 1, wherein the second fluorophore provides the baseline emission, and wherein said baseline emission is used for normalization of the emission measurement from the first fluorophore.

19. The assay of claim 14, wherein the protecting portion provides a baseline emission, and wherein said baseline emission is used for normalization of a further emission from the protected portion.

* * * * *